United States Patent [19]

Isa et al.

[11] 4,270,925

[45] Jun. 2, 1981

[54] METHOD AND APPARATUS FOR AUTOMATICALLY DETERMINING CHLORINE AND CHLORINE DIOXIDE CONCENTRATIONS

[75] Inventors: Isao Isa, Misato; Makoto Ebisawa, Kiryu; Noriyuki Goto, Shinto, all of Japan

[73] Assignee: The Japan Carlit Co., Ltd., Tokyo, Japan

[21] Appl. No.: 49,187

[22] Filed: Jun. 15, 1979

[30] Foreign Application Priority Data

Jun. 24, 1978 [JP] Japan .................................. 53/75956
Oct. 24, 1978 [JP] Japan ................................. 53/130036
Nov. 2, 1978 [JP] Japan ................................. 53/134487

[51] Int. Cl.³ ...................... G01N 33/18; G01N 31/08
[52] U.S. Cl. ............................... 23/230 R; 23/230 A; 73/23.1; 422/62; 422/69
[58] Field of Search ............. 23/230 R, 232 C, 230 A; 422/69, 62

[56] References Cited

U.S. PATENT DOCUMENTS

| | | | |
|---|---|---|---|
| 2,385,471 | 9/1945 | Scharer | 23/230 R |
| 2,783,135 | 2/1957 | Löschbrandt | 23/230 R |
| 3,127,254 | 3/1964 | Astrup et al. | 23/230 B UX |
| 3,149,941 | 9/1964 | Barnitz et al. | 23/232 C UX |
| 3,413,199 | 11/1968 | Morrow | 23/230 R X |
| 3,849,070 | 11/1974 | Garza et al. | 23/230 R |
| 3,966,413 | 6/1976 | Marinenko | 23/230 R X |
| 3,973,915 | 8/1976 | Raffaele et al. | 23/230 B X |
| 4,049,382 | 9/1977 | Ross et al. | 23/230 R |
| 4,092,115 | 5/1978 | Rupe et al. | 23/230 R |

*Primary Examiner*—Barry Richman
*Attorney, Agent, or Firm*—Frishauf, Holtz, Goodman & Woodward

[57] ABSTRACT

Concentration of chlorine and chlorine dioxide in either one or both of a gaseous mixture or an aqueous solution is automatically determined by using a gas-liquid chromatograph and a microcomputer with or without a gas-liquid phase equilibrator.

6 Claims, 3 Drawing Figures

METHOD AND APPARATUS FOR AUTOMATICALLY DETERMINING CHLORINE AND CHLORINE DIOXIDE CONCENTRATIONS

BACKGROUND OF THE INVENTION

1. Field of the Invention

This invention relates to a method and an instrument for automatically determining the concentration of chlorine and chlorine dioxide in either one or both of a gaseous mixture or an aqueous solution.

2. Description of Prior Art

Chlorine dioxide is a commercially important material in such fields as pulp bleaching, water treatment and fat decoloring, and also has recently been used for the denitration of industrail waste gases and removal of phenols from industrial sewage.

One of the methods for generating chlorine dioxide is to reduce a chlorate with a reducing agent in a strong acid. The reactions which occur are exemplified below, wherein, for the sake of illustration, the chlorate used is sodium chlorate and the reducing agent is hydrochloric acid.

  (1)

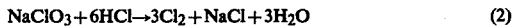  (2)

Chlorine dioxide is formed by reaction (1), but not formed by reaction (2) which competes with reaction (1). It is well known in the field of this invention that the production of chlorine dioxide decreases as the chlorate-to-reducing agent molar ratio and the acid concentration of the reaction medium decreases. The respective concentrations of chlorine and chlorine dioxide in a gaseous mixture removed from a chlorine dioxide generator are determined so as to keep the production high and to prevent the chlorine dioxide from exploding.

Since chlorine dioxide is explosive and highly poisonous and, therefore, hazardous, it is generally absorbed by water and then is used as an aqueous solution in such fields as pulp bleaching and so on. In order to introduce a known controlled amount of chlorine and chlorine dioxide for a pulp bleaching plant, it is always required to determine the respective concentrations of chlorine and chlorine dioxide in such an aqueous solution.

The conventional, generally used procedure for determining the concentrations of chlorine and chlorine dioxide either in a gaseous mixture or in an aqueous solution is the iodimetric procedure in which iodine formed by reaction between iodide ion and chlorine or chlorine dioxide is titrated with sodium thiosulfate. This procedure, however, requires much manpower and much time, and sometimes it is not accurate. The need for a fully automatically controlled process for generating chlorine dioxide is being increasingly recognized these days. With the above in mind, an automatic process analyzer for continuously monitoring chlorine and chlorine dioxide in process fluids has been desired in order to generate and use chlorine dioxide without any danger of explosion and any loss of efficiency.

SUMMARY OF THE INVENTION

It is an object of the invention, therefore, to provide a method and an apparatus for automatically determining the respective concentrations of chlorine and chlorine dioxide in either one or both of a gaseous mixture or an aqueous solution.

It is another object of the invention, to provide an automatic process analyzer for continuously monitoring chlorine and chlorine dioxide in a process for generating or using chlorine dioxide.

Other objects and advantages of the present invention may become apparent to those skilled in the art from the following description and disclosure.

DESCRIPTION OF THE PREFERRED EMBODIMENT

Figure 1:
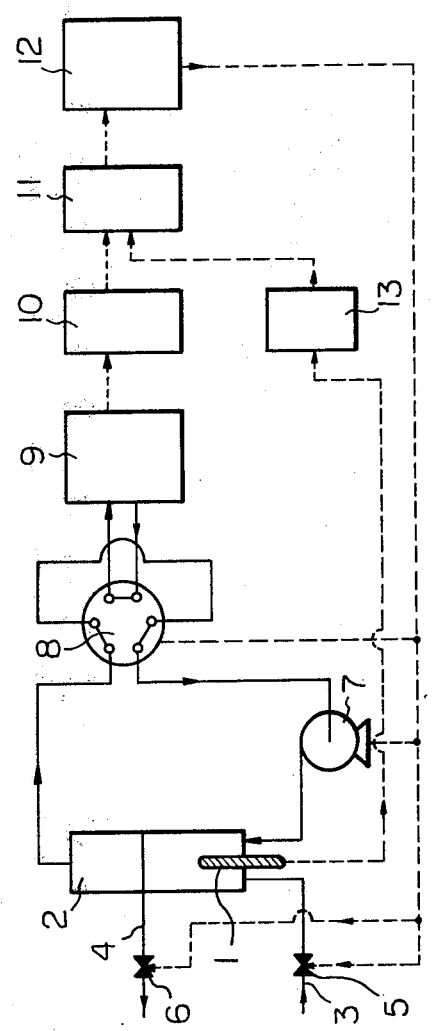
FIG. 1 is a simplified diagram of an automatic analyzer in accordance with this invention.

This invention relates to a method and an apparatus for automatically determining the respective concentrations of chlorine and chlorine dioxide in either one or both of a gaseous mixture or an aqueous solution comprising a step of introducing at least a portion of such a chlorine and chlorine dioxide-containing aqueous solution into a gas-liquid phase equilibrator equipped with a temperature sensing means, a step of introducing the gas phase of said gas-liquid phase equilibrator or at least a portion of such a gaseous mixture through a sample valve into a gas-liquid chromatograph equipped with a column for separating air, chlorine and chlorine dioxide from each other and with a thermal conductivity detector, and a step of introducing the output signals of said gas-liquid chromatograph through a variable gain amplifier and an A/D converter into a microcomputer which calculates the concentrations of chlorine and chlorine dioxide in either one or both of such a gaseous mixture or an aqueous solution, and, then, on the basis of said calculation also regulates the stream of either one or both of the gaseous mixture or an aqueous solution and also regulates said variable gain amplifier so that all the steps referred to above can be conducted automatically.

The gas-liquid phase equilibrator used in the method of this invention has a gas phase and a liquid phase in contact with each other and is so constructed as to enable easily accomplishing gas-liquid equilibrium by such contact between the gas phase and the liquid phase. For example, contact can be realized by pumping the gas phase or the liquid phase through the other or by vibrating said gas-liquid phase equilibrator itself.

Said temperature sensing means is generally selected from the group consisting of a platinum wire resister, a thermocouple, a semiconductor device and a thermistor.

The temperature in said gas-liquid phase equilibrator is kept from 0° to 40° C. If the temperature drops below 0° C., the aqueous solution containing chlorine and chlorine dioxide in said gas-liquid phase equilibrator may freeze. On the other hand, if the temperature goes above 40° C., the analytical results obtained may be erroneous, since chlorine dioxide may be decomposed at such a high temperature according to the following equation:

  (3)

The packing of said column for separating air, chlorine and chlorine dioxide from each other comprises a support and a stationary liquid. The support is generally selected from the group consisting of diatomaceous earth, activated alumina and polyfluorocarbon beads. The stationary liquid is generally selected from the group consisting of polyfluorocarbon oils, silicone greases, silicone oils, and polychlorobiphenyls and mixtures thereof. The preferred stationary liquid is a polyfluorocarbon oil or polychlorobiphenyl.

Said variable gain amplifier used in the method of this invention is to amplify the output signals of the gas-liquid chromatograph that have each different voltage with an amplifier. In fact for a gaseous mixture removed from a generator for chlorine dioxide comprising 80-95% air, 5-15% chlorine dioxide and 0-8% chlorine, the output signals of a gas-liquid chromatograph for air, chlorine dioxide and chlorine will be about 1 V, about 10-40 mV and about 0-20 mV, respectively. If these output signals are amplified by a single amplification degree, the linearity of the amplifier will become poor and its output will be saturated. Analog signals from said variable gain amplifier are changed to digital signals by an A/D converter.

The method for calculating the concentrations of chlorine and chlorine dioxide in accordance with this invention is described below.

The concentrations of chlorine and chlorine dioxide in a gaseous mixture or the gas phase of said gas-liquid phase equilibrator is calculated by $K_1B$ and $K_2C$, respectively. $K_1$ is the slope of the calibration curve corresponding to the concentration of chlorine and B. $K_2$ is the slope corresponding to the concentration of chlorine dioxide and C. B and C are the values integrating the output signals with respect to time for chlorine and chlorine dioxide, respectively. If more accurate analytical values are desired, the concentrations of chlorine and chlorine dioxide are calculated by $K_3B/A$ and $K_4C/A$, respectively. $K_3$ and $K_4$ are the slopes of the calibration curves corresponding to the concentration of chlorine and B/A, and corresponding to that of chlorine dioxide and C/A, respectively. A is the value integrating the output signals with respect to time for air.

The concentration of chlorine dioxide in an aqueous solution is found by multiplying the Henry constant (h) by the concentration of chlorine dioxide in the gas phase of said gas-liquid phase equilibrator. The Henry constant (h) changing with temperature in said gas-liquid phase equilibrator is automatically corrected by the microcomputer by referring to the output of a temperature sensing means.

The relationship between the concentration of chlorine in a gas phase and that of chlorine in an aqueous solution in contact with each other is not proportional. Therefore, a complicated method of calculation is necessary to find the concentration of chlorine in the liquid phase from that of chlorine in the gas phase. If the aqueous solution containing chlorine is acidified with an acid, the relationship between the concentration of chlorine in the gas phase and that of chlorine in the liquid phase becomes proportional. In such a case, therefore, the concentration of chlorine in the liquid phase can be calculated by the method for chlorine dioxide described above.

The acid which is added to the aqueous solution containing chlorine in accordance with this invention can be an inorganic or organic acid which does not react with chlorine. The preferred acid is selected from the group consisting of hydrochloric acid, sulphuric acid, phosphoric acid, nitric acid, perchloric acid, formic acid, acetic acid, oxalic acid and a mixture of two or more thereof.

The acidity of such an acidified aqueouss solution containing chlorine may be from 0.01 to 1 N. If it is below 0.01 N, the relationship between the concentration of chlorine in the gas phase and that of chlorine in the liquid phase is not proportional. On the other hand, when it is above 1 N, there is no particular advantage.

Figure 3:
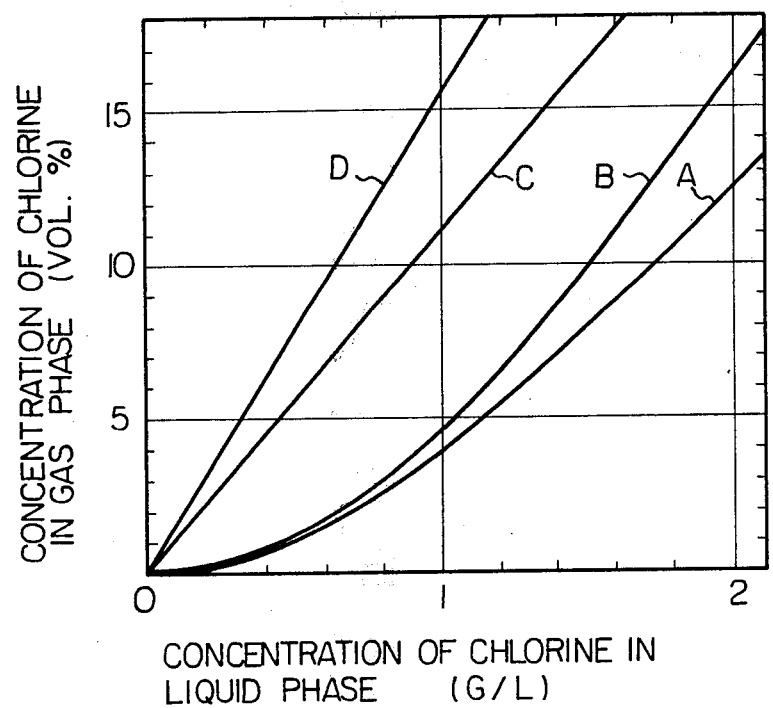
FIG. 3 shows the equilibrium state of chlorine.

The equilibrium state of chlorine, in case of no addition of any acid, is as curve A (aqueous solution, the temperature of the liquid: 10° C.) and curve B (aqueous solution, the temperature of the liquid: 20° C.) of FIG. 3, and hence does not follow Henry's Law. In contrast, in case of addition of some acid, it is as straight line C (the acidity of the acidic aqueous solution: 0.1 N, the temperature of the liquid: 10° C.) and straight line D (the acidity of the acidic aqueous solution: 0.01 N, the temperature of the liquid: 18° C.) of FIG. 3, and hence follows Henry's Law. The present invention is based on such a property.

The advantages obtained with the present invention are as follows:

The concentration of chlorine and chlorine dioxide in either one or both of a gaseous mixture or an aqueous solution can be automatically determined more quickly and more accurately than by the conventional iodimetric procedures. The concentration of chlorine and chlorine dioxide in process fluids for generating or using chlorine dioxide can be automatically and continuously monitored without manpower and, therefore, such a process can be fully automatically controlled.

The following examples are given to further illustrate this invention, but it should be understood that the invention is by no means limited thereto. On the contrary, they are given only to clarify some of the essential working modes of the present invention.

EXAMPLE 1

Example 1 is described by way of an example with reference to FIG. 1 which is a simplified diagram illustrating one embodiment of this invention.

Aqueous solutions containing chlorine and chlorine dioxide at temperature from 10° C. to 30° C. were introduced into a gas-liquid phase equilibrator (2) through line (3) and were removed through line (4). After a valve (5) and a valve (6) were closed, the gas phase in the gas-liquid phase equilibrator (2) was circulated by a pump (AP032Z, made by IWAKI CO., LTD.) (7) through the sample valve (8). Two ml of the gas in the gas-liquid phase equilibrator (2) were introduced into a gas-liquid chromatograph (9) through a sample valve (8).

Operating conditions of the gas-liquid chromatograph (9) were as follows:

Column packing support: diatomaceous earth 60-80 mesh
stationary liquid: polyfluorocarbon oil 25%
Column: 3 mm $\phi \times 5$ mm stainless steel tubing
Column temperature: 40° C.
Carrier gas: He at a flowrate of 20 ml/min
Detector: Thermal conductivity detector (E121, made by GASUKURO KOGYO CO., LTD.) at a filament carrent of 100 mA The output signals of the gas-liquid chromatograph (9) were sent through a variable gain amplifer (10) and an A/D converter ADC80AG12, made by BURR-BROWN) (11) into a microcomputer (18085A, made by INTEL CORPORATION) (12). On the other hand, the output of a temperature sensing means (13) comprising a platinum wire resistor (R040, made by SHINO WORKS LTD.) inserted in the gas-liquid equilibrator (2) was also supplied through the A/D converter (11) into the microcomputer (12). Concentrations of chlorine dioxide were calculated by the microcomputer (12). The valve (5), the valve (6), the pump (7), sample valve (8) and the variable gain amplifier (10) were controlled by the microcomputer (12).

One sample was analyzed for about five minutes by the method described above.

The results obtained are compared with the results obtained by iodimetry in Table 1 below.

TABLE 1

| Temperature in the gas-liquid phase equilibrator (°C.) | Concentration of chlorine dioxide (g/l) Results obtained by Example 1 $X_1$ | Results obtained by iodimetry $Y_1$ | Relative difference $\dfrac{X_1 - Y_1}{Y_1} \times 100$ (%) |
|---|---|---|---|
|  | 0.57 | 0.57 | 0 |
| 10.5 | 1.02 | 1.03 | 0.97 |
|  | 4.95 | 4.95 | 0 |
|  | 13.95 | 13.11 | 0.15 |
|  | 0.37 | 0.37 | 0 |
| 16.2 | 1.21 | 1.20 | 0.83 |
|  | 6.30 | 6.32 | 0.32 |
|  | 12.55 | 12.52 | 0.24 |
|  | 0.73 | 0.73 | 0 |
| 20.0 | 1.58 | 1.58 | 0 |
|  | 4.32 | 4.35 | 0.69 |
|  | 14.06 | 14.01 | 0.35 |
|  | 0.25 | 0.25 | 0 |
| 24.7 | 1.03 | 1.04 | 0.96 |
|  | 5.81 | 5.83 | 0.34 |
|  | 12.13 | 12.13 | 0 |
|  | 0.41 | 0.41 | 0 |
| 30.1 | 1.52 | 1.51 | 0.66 |
|  | 5.90 | 5.90 | 0 |
|  | 12.05 | 12.07 | 0.17 |
|  | 0.28 | 0.29 | 0 |
| 34.1 | 0.95 | 0.95 | 0 |
|  | 4.52 | 4.51 | 0.22 |
|  | 9.81 | 9.84 | 0.30 |

EXAMPLE 2

Figure 2:
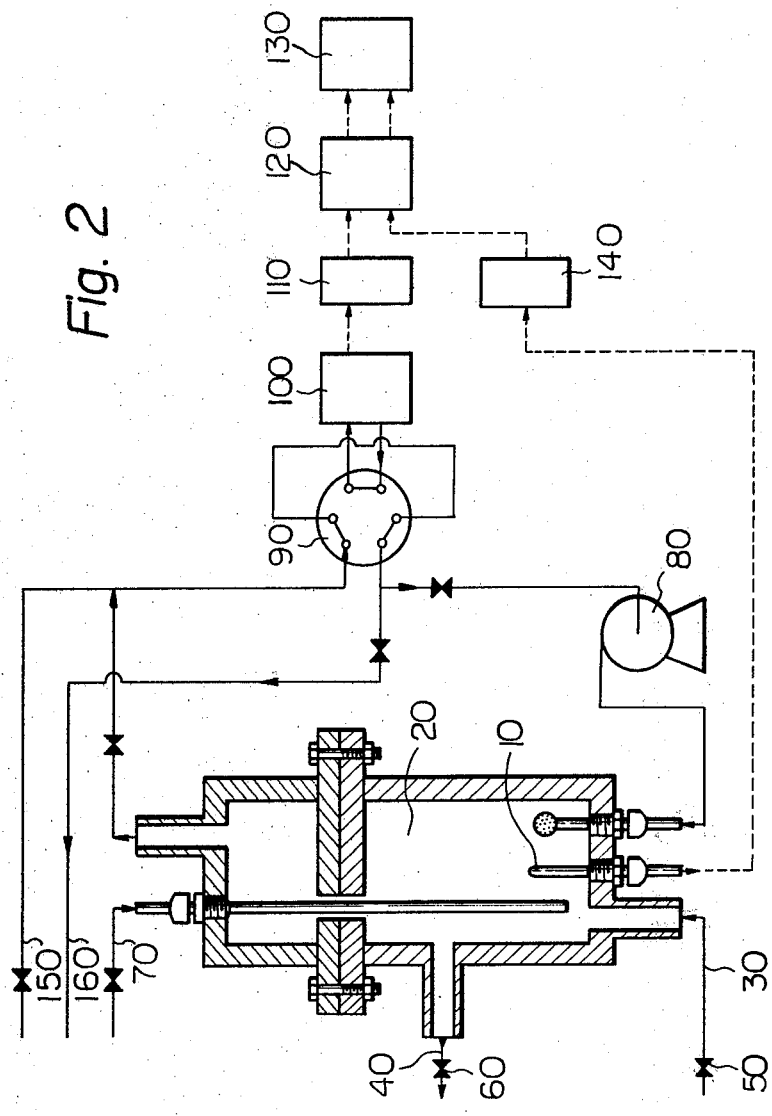
FIG. 2 is a simplified diagram of another automatic analyzer in accordance with this invention.

Example 2 is described with reference of FIG. 2 which is a simplified diagram illustrating one embodiment of this invention.

Aqueous solutions containing chlorine and chlorine dioxide were introduced into a gas-liquid phase equilibrator (20) through line (30) and were removed through line (40). After a valve (50) and a valve (60) were closed, aqueous solutions in the gas-liquid phase equilibrator (20) were acidified by adding hydrochloric acid through line (70). The acidity of the aqueous solutions was 0.1 N. And then the gas phase in the gas-liquid phase equilibrator (20) was circulated by a pump (AP032Z, made by IWAKI CO., LTD.) (80) through the sample valve (90) for about five minutes. One ml of the gas in the gas-liquid phase equilibrator (20) was introduced into a gas-liquid chromatograph (100) through a sample valve (90).

Operating conditions of the gas-liquid chromatograph (100) were as follows:

Column packing support: polyfluorocarbon beads 20-80 mesh stationary liquid: polychlorobiphenyl 15%
Column: 3 mm φ×2 m glass tubing
Column temperature: 60° C.
Carrier gas: He at a flowrate of 20 ml/min
Detector: Thermal conductivity detector (E121, made by GASUKURO KOGYO CO., LTD.) at a filament current of 100 mA The output signals of the gas-liquid chromatograph (100) were sent through a variable gain amplifier (110) and an A/D converter ADC80AG12, made by BURR-BROWN) (120) into a microcomputer (18085A, made by INTEL CORPORATION) (130). On the other hand, the output of the temperature sensing means (140) comprising a thermistor (YSI44011, made by YELLOW SPRINGS INSTRUMENT CO.) (10) inserted in the gas-liquid phase equilibrator (20) was also sent through the A/D converter (120) into the microcomputer (130).

Respective concentrations of chlorine and chlorine dioxide were calculated by the microcomputer (130).

Gaseous mixtures containing chlorine and chlorine dioxide were introduced into the sample valve (90) through line (150) and removed through line (160). The stream of the gaseous mixtures was switched by the sample valve (90) and one ml of the gaseous mixture was introduced into the gas-liquid chromatograph (100). The output signals of the gas-liquid chromatograph (100) were introduced through the variable gain amplifier (110) and the A/D converter (120) into a microcomputer (130). Concentrations of chlorine and chlorine dioxide in the gaseous mixtures were calculated by the microcomputer (130). All valves described in FIG. 2, the pump (80), the sample valve (90) and variable gain amplifier (110) were controlled by the microcomputer (130).

The results obtained are compared with the results obtained by iodimetry in Table 2 and Table 3.

TABLE 2

Concentrations of Chlorine and Chlorine Dioxide in Aqueous Solutions

| Temperature in gas-liquid phase equilibrator (°C.) | Concentration of chlorine (g/l) | | | Concentration of chlorine dioxide (g/l) | | |
|---|---|---|---|---|---|---|
| | Results obtained by Example 2 $X_2$ | Results obtained by iodimetry $Y_2$ | Relative difference $\frac{X_2 - Y_2}{Y_2} \times 100$ (%) | Results obtained by Example 2 $X_3$ | Results obtained by iodimetry $Y_3$ | Relative difference $\frac{X_3 - Y_3}{Y_3} \times 100$ (%) |
| 10.8 | 0.025 | 0.025 | 0 | 0.31 | 0.31 | 0 |
| | 0.109 | 0.108 | 0.92 | 2.44 | 2.45 | 0.41 |
| | 0.275 | 0.277 | 0.73 | 5.72 | 5.72 | 0 |
| | 0.498 | 0.496 | 0.40 | 7.35 | 7.33 | 0.27 |
| | 0.753 | 0.752 | 0.13 | 10.86 | 10.88 | 0.18 |
| | 0.980 | 0.985 | 0.51 | 14.22 | 14.25 | 0.21 |
| 15.2 | 0.035 | 0.035 | 0 | 1.08 | 1.07 | 0.93 |
| | 0.124 | 0.125 | 0.81 | 2.63 | 2.62 | 0.38 |
| | 0.331 | 0.331 | 0 | 4.82 | 4.84 | 0.41 |
| | 0.552 | 0.555 | 0.54 | 7.91 | 7.88 | 0.38 |
| | 0.707 | 0.710 | 0.42 | 9.80 | 9.86 | 0.61 |
| | 1.059 | 1.055 | 0.38 | 10.64 | 10.56 | 0.76 |
| 19.7 | 0.031 | 0.031 | 0 | 1.54 | 1.53 | 0.65 |
| | 0.115 | 0.114 | 0.87 | 3.61 | 3.64 | 0.82 |
| | 0.302 | 0.303 | 0.33 | 4.33 | 4.31 | 0.46 |
| | 0.515 | 0.511 | 0.78 | 7.67 | 7.71 | 0.52 |
| | 0.731 | 0.736 | 0.68 | 8.85 | 8.90 | 0.56 |
| | 0.998 | 0.995 | 0.30 | 11.12 | 11.05 | 0.63 |

TABLE 3

Concentrations of Chlorine and Chlorine Dioxide in Gaseous Mixtures

| Concentration of chlorine (volume %) | | | Concentration of chlorine dioxide (volume %) | | |
|---|---|---|---|---|---|
| Results obtained by Example 2 $X_4$ | Results obtained by iodimetry $Y_4$ | Relative difference $\frac{X_4 - Y_4}{Y_4} \times 100$ (%) | Results obtained by Example 2 $X_5$ | Results obtained by iodimetry $Y_5$ | Relative difference $\frac{X_5 - Y_5}{Y_5} \times 100$ (%) |
| 1.60 | 1.59 | 0.63 | 1.23 | 1.23 | 0 |
| 2.02 | 2.00 | 1.0 | 3.65 | 3.62 | 0.83 |
| 2.94 | 2.94 | 0 | 5.21 | 5.19 | 0.39 |
| 3.76 | 3.78 | 0.53 | 6.11 | 6.16 | 0.81 |
| 4.55 | 4.51 | 0.89 | 8.63 | 8.68 | 0.58 |
| 5.63 | 5.60 | 0.54 | 9.92 | 9.90 | 0.20 |

What is claimed is:

1. A method for automatically determining the respective concentrations of chlorine and chlorine dioxide in an aqueous solution comprising the following steps:

(a) feeding a portion of a chlorine and chlorine dioxide containing aqueous solution into a gas-liquid phase equilibrator at 0° C. to 40° C. and measuring the temperature of the liquid phase in said gas-liquid phase equilibrator by a temperature sensing means;

(b) feeding the gas phase of said gas-liquid phase equilibrator through a sample valve into a gas-liquid chromatograph;

(c) separating the gas phase in said gas-liquid chromatograph into air, chlorine and chlorine dioxide by a column which comprises a support selected from the group consisting of diatomaceous earth, activated alumina and polyfluorocarbon beads and a stationary liquid selected from the group consisting of polyfluorocarbon oil, silicone oil and polychlorobiphenyl;

(d) determining the respective thermal conductivities of said separated air, chlorine and chlorine dioxide with a thermal conductivity detector, and generating electrical signals which respectively correspond to said thermal conductivities;

(e) passing said electrical signals through a variable gain amplifier for amplifying said electrical signals to substantially similar levels, and thereafter through an A/D converter;

(f) feeding the outputs of said A/D converter and said temperature sensing means to a micro-computer which calculates the respective concentrations of chlorine and chlorine dioxide in aqueous solution utilizing a correction factor determined from the output of said temperature sensing means; and (g) regulating the feeding of such aqueous solution into said equilibrator and also said variable gain amplifier by said micro-computer.

2. The method of claim 1, wherein the aqueous solution in said gas-liquid phase equilibrator is acidified to from 0.01 N to 0.1 N with an acid which is selected from the group consisting of hydrochloric acid, sulphuric acid, phosphoric acid, nitric acid, perchloric acid, formic acid, acetic acid, oxalic acid and a mixture of two or more thereof.

3. The method of claim 1, wherein said temperature sensing means is a platinum wire resistor.

4. The method of claim 1, wherein said temperature sensing means is a thermocouple.

5. The method of claim 1, wherein said temperature sensing means is a semiconductor device.

6. The method of claim 1, wherein said temperature sensing means is a thermistor.

* * * * *